United States Patent [19]
Meier

[11] Patent Number: 6,154,674
[45] Date of Patent: Nov. 28, 2000

[54] SELF-CALIBRATING ADAPTIVE-RATE CARDIAC PACEMAKER

[75] Inventor: Jan H. Meier, Uttenreuth, Germany

[73] Assignee: Biotronik Mess-und Therapiegeraete GmbH & Co. Ingenieurbuero Berlin, Berlin, Germany

[21] Appl. No.: 09/239,995

[22] Filed: Jan. 29, 1999

[30] Foreign Application Priority Data

Jan. 29, 1998 [DE] Germany .......................... 198 04 843

[51] Int. Cl.$^7$ .................................................. A61N 1/365
[52] U.S. Cl. ............................................. 607/23; 607/18
[58] Field of Search .................................. 607/18, 20, 23

[56] References Cited

U.S. PATENT DOCUMENTS

| | | | |
|---|---|---|---|
| 5,063,927 | 11/1991 | Webb et al. ............................... | 607/20 |
| 5,065,759 | 11/1991 | Begemann et al. . | |
| 5,074,302 | 12/1991 | Poore et al. . | |
| 5,133,349 | 7/1992 | Heinze . | |
| 5,292,340 | 3/1994 | Crosby et al. . | |
| 5,303,702 | 4/1994 | Bonnet et al. . | |

FOREIGN PATENT DOCUMENTS

| | | |
|---|---|---|
| 0 059 868 | 9/1982 | European Pat. Off. . |
| 0 249 818 | 12/1987 | European Pat. Off. . |
| 0 310 216 | 4/1989 | European Pat. Off. . |
| 1 325 851 | 8/1989 | European Pat. Off. . |
| 0 361 517 | 9/1989 | European Pat. Off. . |

(List continued on next page.)

OTHER PUBLICATIONS

Max Schaldach, *Electrotherpay of the Heart*, pp. 113–121, Jan., 1992.

Urbaszel et al., *Measurement of Intracardiac Impedance to Determine Sympathetic Activity in Rate–Responsive Pacing—Part 1: Biomedical and Technical Basis*, Biomedizinische Technik, vol. 37, Issue 7, pp. 155–161, Aug. 1992.

*Primary Examiner*—George R. Evanisko
*Attorney, Agent, or Firm*—Venable; George H. Spencer; Robert Kinberg

[57] ABSTRACT

A self-calibrating adaptive-rate cardiac pacemaker having a measuring and processing device for measuring the course over time of a physiological variable over a predetermined portion of a heart cycle and for obtaining a course parameter from the course over time, a stimulation parameter determining device downstream of the measuring and processing device and controlled by a sequence controller for determining a stimulation parameter value, in particular the adaptive stimulation rate, a body sensor connected to one input of the stimulation parameter determining device, for detecting an exertion variable, whose signal is used jointly with the course parameter to determine the stimulation parameter value, and a stimulator unit for generating and outputting stimulation pulses at the determined stimulation parameter value. The measuring and processing device is arranged to obtain a plurality of different values of the course parameter as a function of at least one setting point in a calibration phase, and the stimulation parameter determining device has a stimulation parameter calculating device connected downstream of the measuring and processing device for calculating a plurality of stimulation parameter selection values, each as a function of one value for the course parameter, a reference parameter calculating device connected downstream of the body sensor, for calculating an activity-determined reference parameter value, a comparator unit connected on the input side to the stimulation parameter calculating device and to the reference parameter calculating device, for comparing the parameter selection values with the reference parameter value, and a decision-making device connected on the input side to the output of the comparator unit, for selecting one of the setting point values of the measuring and processing device, associated with the parameter selection values, as current setting point value for further control of the pacemaker, substantially on the basis of the course parameter as the outcome of the comparison.

9 Claims, 3 Drawing Sheets

FOREIGN PATENT DOCUMENTS

| | | |
|---|---|---|
| 0 151 689 | 12/1990 | European Pat. Off. . |
| 0 532 149 | 4/1992 | European Pat. Off. . |
| 0 498 533 | 8/1992 | European Pat. Off. . |
| 92/16256 | 10/1992 | European Pat. Off. . |
| 93/20889 | 10/1993 | European Pat. Off. . |
| 0 654 285 | 5/1995 | European Pat. Off. . |
| 0 702 980 | 3/1996 | European Pat. Off. . |
| 0 793 976 | 9/1997 | European Pat. Off. . |
| 0 796 636 | 9/1997 | European Pat. Off. . |
| 0 804 941 A2 | 11/1997 | European Pat. Off. . |
| 0 804 941 A3 | 12/1998 | European Pat. Off. . |
| 42 31 601 | 3/1994 | Germany . |
| 44 47 447 | 7/1996 | Germany . |
| 196 09 411 | 9/1997 | Germany . |

SELF-CALIBRATING ADAPTIVE-RATE CARDIAC PACEMAKER

CROSS-REFERENCE TO RELATED APPLICATION

This application claims the priority of German Patent Application No. 198 04 843.2 filed Jan. 29, 1998, the subject matter of which is incorporated herein by reference.

FIELD OF THE INVENTION

The present invention relates to a self-calibrating adaptive-rate cardiac pacemaker having a measuring and processing device for measuring the course over time of a physiological variable over a predetermined portion of a heart cycle and for obtaining a course parameter from the course over time, a stimulation parameter determining device arranged downstream of the measuring and processing device and controlled by a sequence controller for determining a stimulation parameter value, in particular the adaptive stimulation rate, a body sensor connected to one input of the stimulation parameter determining device, for detecting an exertion variable, whose signal is used jointly with the course parameter to determining the stimulation parameter value, and a stimulator unit for generating and outputting stimulation pulses at the determined stimulation parameter value.

BACKGROUND OF THE INVENTION

Adaptive-rate cardiac pacemakers in which the stimulation frequency or rate is set as a function of signals picked up in the body of the patient that reflect the physiological requirements of the patient with regard to cardiac activity have been known and been in clinical use for years in many versions. A survey of the goals pursued in the development of rate adaptation in pacemaker technology and the relevant paths taken is given in K. Stangl et al, Frequenzadaptive Herzschrittmacher [Adaptive-Frequency Cardiac Pacemakers], Darmstadt, 1990.

Many arrangements for measuring impedance in the area of the chest or the heart to obtain an impedance signal for adaptive-rate cardiac pacemakers are also known, and thus the technology of intracardial impedance measurement per se is familiar to one skilled in the art. Most of these arrangements are designed to obtain a signal that represents the tidal volume or the cardiac output as an expression of the patient's physical exertion level and as an actual rate control parameter; for this aspect, see for instance European Patent Disclosures EP 0 151 689 B1 and EP 0 249 818, or German Patent Disclosure DE 42 31 601 A1.

The so-called ResQ method (for Regional Effective Slope Quality) is also known (Max Schaldach, Electrotherapy of the Heart, First Edition, Springer-Verlag, pp. 114 ff.), in which the course over time of intracardial impedance is used to determine the physiologically appropriate adaptive heart rate.

This method is based on the recognition that the intracardial impedance has an especially significant dependency on the exertion level of the organism within a certain time slot after a QRS complex—the so-called "region of interest" or ROI.

The slope of the impedance curve in the ROI is therefore determined, and the difference between the slope of a resting or reference curve and the slope of the currently measured impedance curve (exertion curve) is calculated. The adaptive heart rate is set as a function of this difference. The association of the calculated slope difference with the heart rate to be set is done here as well by means of a characteristic curve. Since this curve differs for different people and is dependent on the physical condition, the cardiac pacemaker must be calibrated individually for each patient, and the calibration must be repeated if the patient's health and capacity for exertion changes, or if his life circumstances change, and in that case then the location of the ROI must be checked as well.

Various suggestions for self-adaptation (autocalibration) of adaptive-rate cardiac pacemakers are found in European Patent Disclosure EP 0 325 851 A2, U.S. Pat. No. 5,074,302, or European Patent Disclosure EP 0 654 285 A2. U.S. Pat. No. 5,303,702 shows a trend calculation for the self-adaptation of a pacemaker controlled on the basis of the cardiac output.

International Patent Disclosure WO 93/20889 shows a two-sensor arrangement with one circuit for detecting the cardiac output and with an additional activity sensor, in which the stimulation rate is determined as a function of the target rates that can be derived for the individual sensors.

European Patent Application EP 97 250 057.3 shows an impedance-controlled pacemaker is proposed, which is capable of making do without a patient-specific calibration and adapts automatically to altered peripheral conditions. In this pacemaker, the time integral of the impedance over a predetermined portion of the heart cycle is determined as a primary impedance variable and used for rate adaptation.

OBJECT AND SUMMARY OF THE INVENTION

It is the object of the present invention to provide a cardiac pacemaker of the above type that functions reliably in self-calibrating fashion, at acceptable expense for calculation and acceptable current consumption.

This object is achieved by a cardiac pacemaker of the above type whereas the measuring and processing device is arranged to obtain a plurality of different values of the course parameter as a function of at least one setting point in a calibration phase and wherein the stimulation parameter determining device has a stimulation parameter calculating device connected downstream of the measuring and processing device, for calculating a plurality of stimulation parameter selection values each as a function of one value for the course parameter, a reference parameter calculating device connected downstream of the body sensor, for calculating an activity determined reference parameter value, a comparator unit connected on the input side to the stimulation parameter calculating device and to the reference parameter calculating device, for comparing the parameter selection values with the reference parameter value, and a decision-making device connected on the input side to the output of the comparator unit, for selecting one of the setting point values of the measuring and processing device, associated with the parameter selection values, as a current setting point valued for further control of the pacemaker, substantially on the basis of the course parameter as the outcome of the comparison.

The invention encompasses the concept of utilizing the course over time of the relevant physiological variable—especially the intracardial impedance—during a calibration phase to derive a family of model stimulation parameter curves, from which, by comparison with a stimulation parameter curve obtained independently of the detection of the aforementioned parameter value (impedance) the most suitable is chosen for further pacemaker control. As a rule, this will be a curve based on the aforementioned various whose course correlates most strongly with the curve ascertained independently of this variable.

The evaluation of impedance measurements is then done in accordance with the ResQ or slope method sketched above, in such a way that at every instant, n stimulation rate values are calculated on the basis of n different pairs of scanning times along the impedance curve. The time dependency of the rate values pertaining to a fixed pair of scanning times in each case forms a model stimulation rate curve from which a selection can be made.

In a preferred version, the cardiac pacemaker of the invention evaluates the intracardial impedance, in particular the right-ventricular impedance measured in unipolar fashion, over a wide range, which typically includes the ROI regions set for individual patients. The pairs of scanning times are also preprogrammed in such a way that they will be certain to contain the "optimal" pair for the applicable patient. Defining them, however, does not require patient-specific programming after implantation; instead, they are preferably stored in memory in a read only memory when the pacemaker is manufactured.

The characteristic curve that determines the dependency of the stimulation rate on the impedance variable and that is an essential operating parameter of the rate determining device is not necessarily static but can instead be optimized continuously or at certain time intervals, in order in particular to attain an adaptation in the range of variation of the impedance variable to the allowable variation range of the heart rate.

In this version, the variation range is not known at the onset of operation but instead is ascertained during operation by ongoing measurement of the impedance and then optimized after each measurement. At the onset of operation, an estimated value for the lower and upper limit values of the variation range is specified as a starting value.

In the setting, two cases can then be distinguished: First, a measured value for the impedance can exceed the previously ascertained variation range either at the top or the bottom. In that case, the variation range is widened accordingly and thus updated. The time constant of this adaptation operation is preferably on the order of magnitude of a few second, to achieve fast adaptation and to prevent a heart rate that—however briefly—is excessively high. Second, the case can arise where the impedance, over a relatively long period of time, no longer fully exhausts the previously determined variation range. In that case, the variation range can be reduced again slowly (with a time constant preferably on the order of magnitude of weeks). The stimulation rate/impedance characteristic curve assigns the base rate to the lower limit value for the variation range of the activity variable and corresponding assigns the maximum stimulation rate to the upper limit value of the activity variable. By varying these limit values during the optimization, the characteristic curve itself consequently changes as well.

Advantageous refinements of the invention are also defined by the dependent claims and will be described in further detail below, along with the description of a preferred embodiment of the invention, in conjunction with the drawings.

DESCRIPTION OF THE PREFERRED EMBODIMENT

Figure 1:
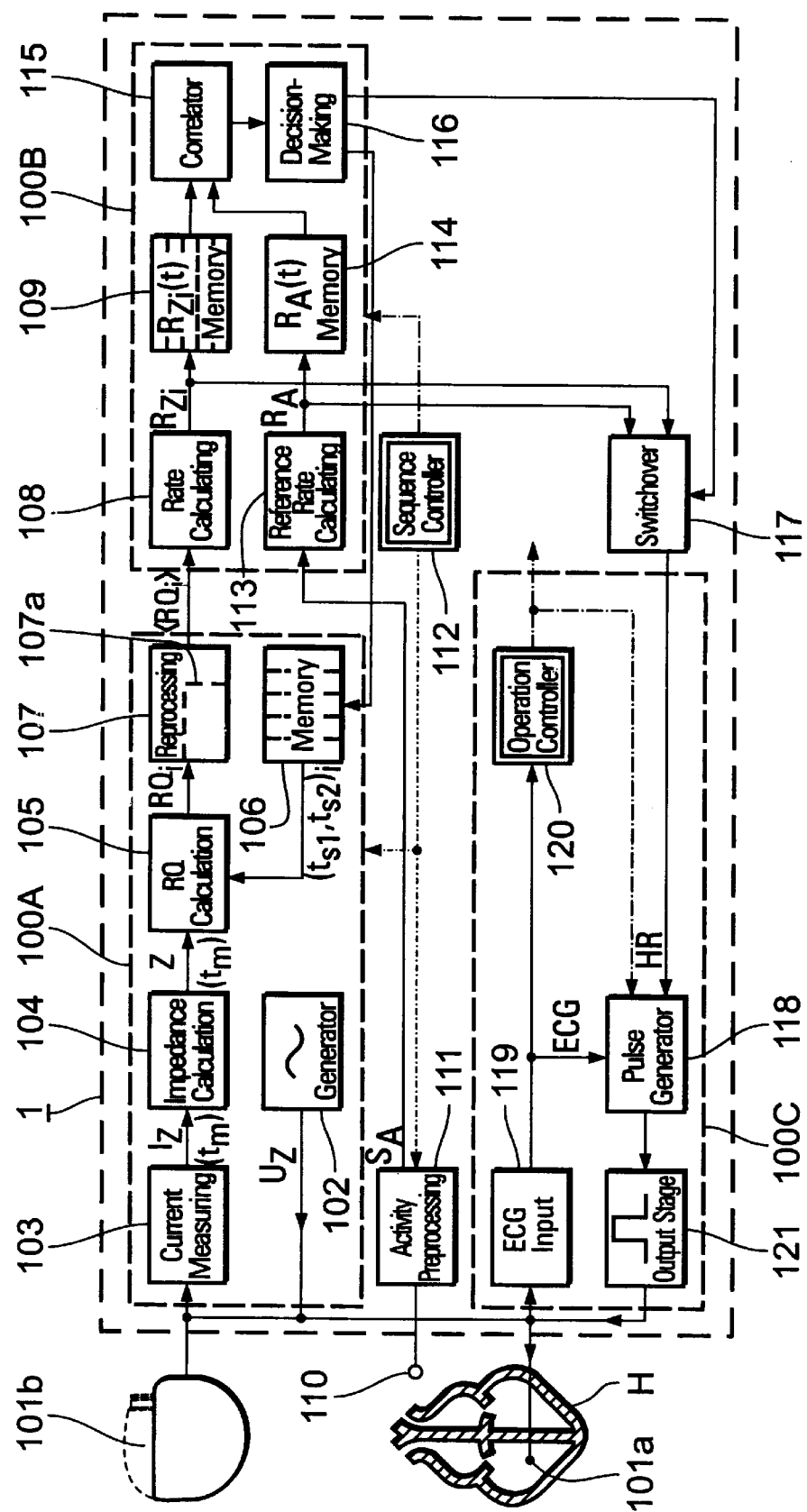
FIG. 1 is a block circuit function diagram for a cardiac pacemaker as an exemplary embodiment of the invention.

As the exemplary embodiment of the invention, FIG. 1 shows an adaptive-rate cardiac pacemaker 100 in the form of a fragmentary block circuit function diagram, in which only the components important to describing the invention are shown. The layout otherwise is like the known cardiac pacemaker.

The cardiac pacemaker 100 has a unipolar pacemaker and measuring electrode 101a in the right ventricle of the heart H for detecting heart signals, measuring the right-ventricular intracardial impedance Z, and as a stimulation electrode. A housing electrode 101b acts as a counterelectrode.

The impedance measurement is effected in a manner known per se in clocked form, by imposing a measurement voltage on the electrode 101a via a measurement voltage generator 102 and by measuring the current $I_z(t_m)$ between the measurement electrode 101a and the counterelectrode 101b at m equidistant preprogrammed times $t_m$ via a current measuring circuit 103. The values $Z(t_m)$ characterizing the course over time of the impedance result, at the output of an impedance calculation stage 104 downstream of the current measuring circuit 103, as quotients of the (fixedly preset) measurement voltage and the measured current values.

In an RQ calculation stage 105, which is connected via a control input to a scanning time memory 106, a selection quantity of n rate control parameter values $RQ_i$ for each detected impedance course over time $Z(t_m)$ is calculated, by dividing the difference $(Z(t_{s1})-Z(t_{s2}))$ of the impedance values for each of n scanning time value pairs $(t_{s1}, t_{s2})_i$ by the associated time interval $(t_{s1}-t_{s2})_i$.

Figure 2:
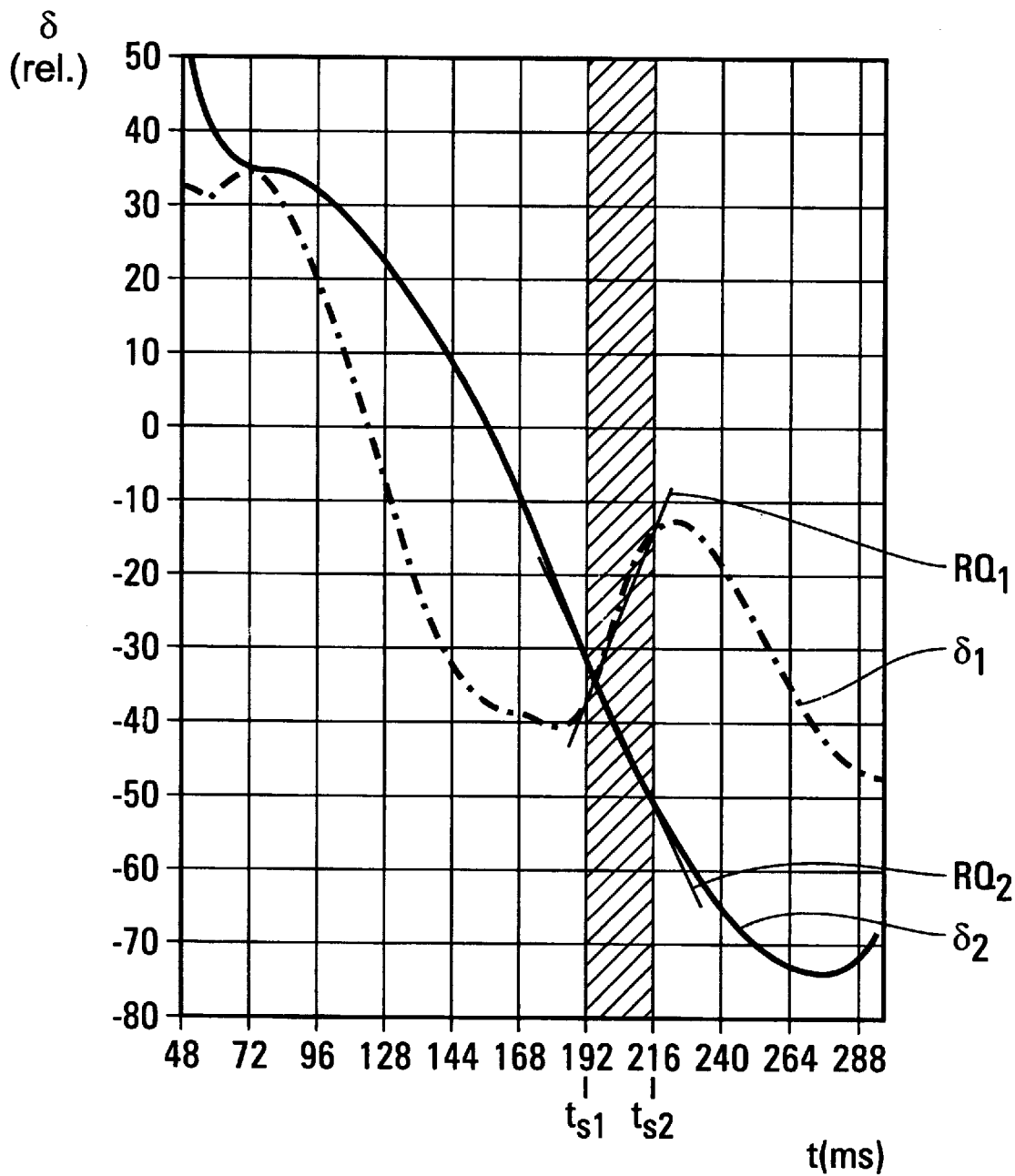
FIG. 2 shows a portion of each of two conductivity measurement curves, picked up intracardially, to illustrate how the impedance variable RQ is obtained in a preferred version of the invention.

In FIG. 2, the conductivity σ measured (in relative units) at a unipolar electrode is plotted for two different exertion states of one patient (solid line=high exertion; dot-dashed line=resting) over the time after an excitation pulse. In the region between the times $t_{s1}$, $t_{s2}$, the curve course differs the most strongly, so that the rises $RQ_1$, $RQ_2$ of the curves in this time region can provide a usable rate control parameter. The rise is approximated by means of the quotient of the difference in the conductivity measured values or the impedance measured values reciprocal to them at the scanning times and their spacing.

In a reprocessing stage 107 downstream of the RQ calculating stage, respiration-dictated abrupt changes from one heartbeat to another in the rate control parameter values causes by corresponding impedance fluctuations are filtered out with the aid of a smoothing algorithm (known per se), and a quantity of smoothed RQ values <$RQ_i$> is available at the output of stage 107. The reprocessing stage 107, for performing the reprocessing, in particular has an internal FIFO working memory 107a, in which in each case in sliding fashion for a predetermined sequence of successive heartbeats, the associated $RQ_i$ values for performing the reprocessing are stored in memory. For stage 107, further functions can be programmed selectively, such as an algorithm for reducing the influence of the so-called orthostasis effect, that is, to partly eliminate irregular impedance fluctuations that are dictated solely by changes of position of the patient and have no significance for rate control.

The components 102–107 described above form an impedance processing device 100A of the pacemaker 100.

Connected downstream of the post processing stage 107 is a rate calculating device 108, in which, on the basis of the smoothed values of the rate control parameters <$RQ_i$>, in accordance with a fixedly programmed algorithm, one impedance-based value $R_{zi}$ of the stimulation rate is calculated at a time. Connected to the output of the rate calculating device 108 is a rate time course memory 109 with n memory regions, in which the time dependencies of the individual impedance-based rate values $R_{zi}(t)$, calculated on the basis of different scanning times, are stored in memory over a predetermined calibration period (see FIG. 3).

The pacemaker 100 is assigned an activity sensor 110, whose signals are subjected in a manner are subjected in a manner known per se to amplification and filtration in an activity signal preprocessing stage 111.

A rate determining sequencer 112 controls both the impedance detection and evaluation, described above, in stage 100A and the activity signal detection and evaluation. The impedance measurements and activity detections are tripped by the sequence controller 112 at times preprogrammed in an internal timing program memory within a 24-hour calibration period, and the impedance measurements are moreover tripped in synchronism with stimulated or spontaneous cardiac events. The repetition period of the calibration cycles is also programmed internally in the sequencer 112.

The preprocessed activity signal $S_A$ is delivered to a reference rate calculating stage 113, where in accordance with an algorithm known per se an activity-based value $R_A$ for the stimulation rate is calculated. In a reference rate time course memory 114, connected downstream of the stage 113 and also having n memory regions, the time dependency of the activity-based calculated rate values $R_A(t)$ over the calibration period (see again FIG. 3) is stored in memory.

The rate time course memory 109 and the reference rate time course memory 114 are connected to the two signal inputs of a correlator stage 115, in which the n correlation coefficients of the individual impedance-based rate time dependencies $R_{zi}(t)$ are ascertained with regard to the reference rate time course $R_A(t)$. The output of the correlator stage 115 is connected to a decision-making device 116, in which the maximum value of the transient fluctuation is determined, and the scanning time value pair $(t_{s1}, t_{s2})_j$ for which the time dependency of the rate correlates most strongly with the time dependency of the rate calculated on the basis of the activity signal is defined as the optimal pair for the impedance-based rate calculation.

Figure 3:
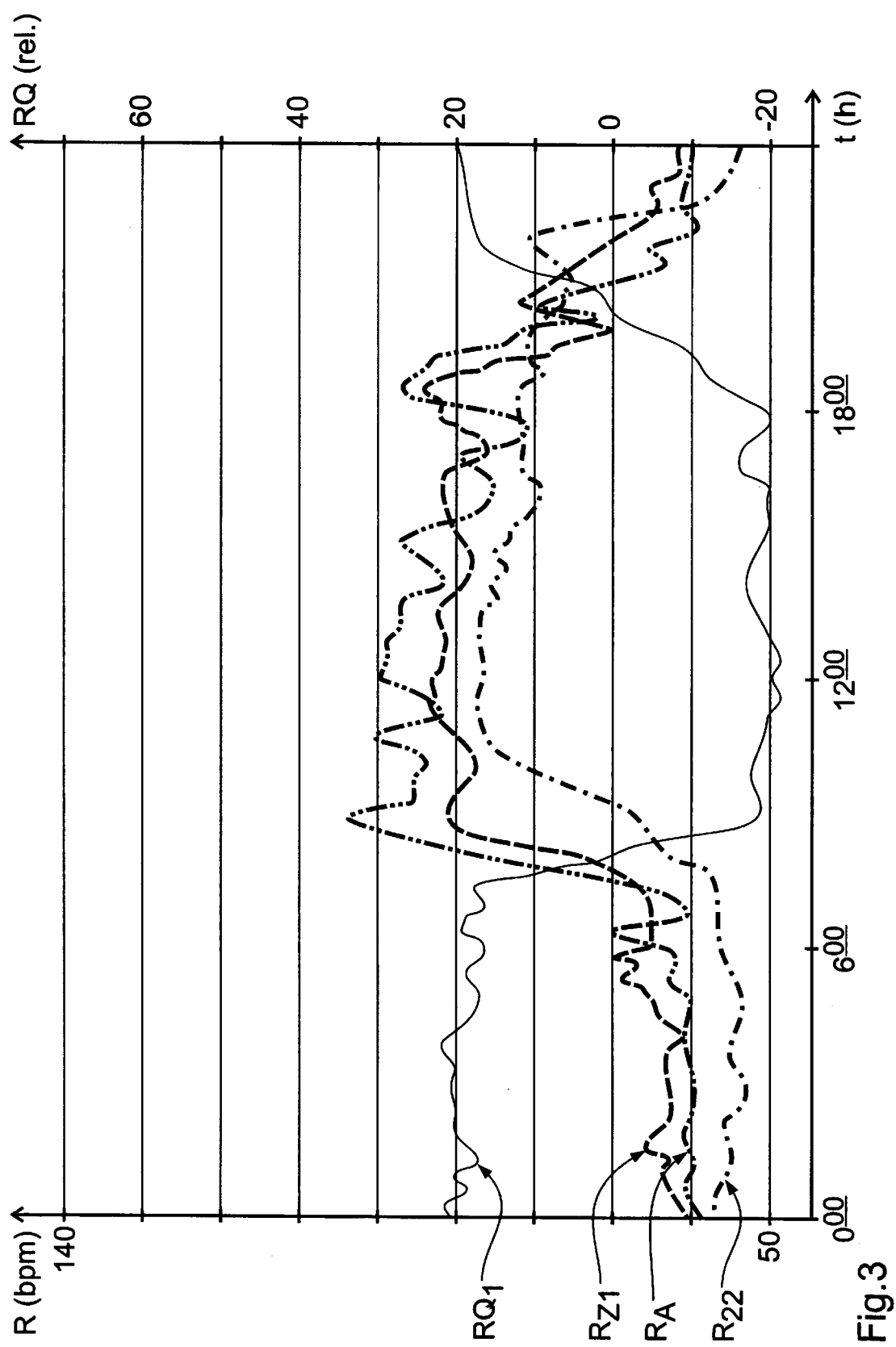
FIG. 3 is a comparison diagram which shows the course over time of a reference stimulation rate, calculated on the basis of activity signals, and two selection stimulation rates, calculated on the basis of impedance signals with different settings of the RQ calculation points in FIG. 2.

In FIG. 3, two time courses by way of example of stimulation rates $R_{Z1}$, $R_{Z2}$ calculated on the basis of impedance are compared with the time course of the rate $R_A$ calculated on the basis of activity. FIG. 3 also shows an example (in the form of a curve drawn in a fine solid line) for the course over time of a rate control parameter RQ; this time dependency, however, is not ascertained cohesively per se in the arrangement described here. Of the two impedance-based curves shown, that for $R_{Z1}$ clear has the higher transient fluctuation, at $R_a$.

The stages 108, 109 and 113–116 together form the rate determining device 100B of the pacemaker.

The decision-making device 116 outputs a corresponding control signal to the memory access controller of the scanning time memory 106, on the basis of which, for subsequent pacemaker operation (until the next calibration procedure), only this $j^{th}$ pair of values is made the basis for ascertaining the rate control parameter $RQ_j$. Furthermore, a control signal is output to a rate control switchover unit 117, at whose two signal inputs the output signal $R_{zj}$ of the (impedance-based) rate calculating device 108 and that of the (activity-based) reference rate calculating device 113 are applied. In the rate control switchover unit 117, once the result of calibration is available, a switchover is made from the activity-based rate control of current pacemaker operation, which is established during the calibration phase, to the impedance-based rate control.

The current rate value HR present at the output of the switchover unit 117 is delivered to a stimulation pulse generator 118, which together with an ECG input stage 119, a pacemaker operation controller 120, and an output stage 121, as well as other components known per se, forms the actual pacemaker block 100C. The function of these components is assumed here to be known per se.

It should be noted that the signal connection shown in FIG. 1 of the pacemaker controller 120 to the measuring electrode 101a, with which the heart actions or intracardial ECGs are also detected, makes it possible to distinguish between spontaneous and evoked cardiac actions and thus to take into account the type of event in the impedance-based rate calculation. In particular, the calculated stimulation rate can have a rate offset added to it each time the event type changes; the amount of which the is selected, as a function of the former rate value and the current rate value, such that the rate jump does not exceed a predetermined amount, and in subsequent cardiac events this offset is gradually reduced to zero again. The specific circuitry means for realizing this additional function are available to one skilled in the art from known arrangements for rate smoothing or rate adaptation.

The invention is not limited in its embodiment to the preferred exemplary embodiments described above. On the contrary, a number of variants that make use of the claimed embodiment even in another kind of version are also conceivable.

For instance, instead of the activity sensor, some other sensor can be used for calibration that furnishes a physiological variable representing the exertion of the patient.

For taking the orthostasis effect into account in an improved way, a position sensor can additionally be provided, whose signals, via a suitable algorithm, affect the processing of the impedance signal. As an alternative to this last refinement, the correlation determination can be done with reduced weighting of the impedance values picked up in resting phases compared with the curve components in exertion phases, because the orthostasis effect is most problematic in resting phases.

A predetermined period of time need not necessarily be adhered to in the calibration; instead, the calibration can also be ended once a predetermined threshold value for the correlation variable is reached. Besides saving electrical energy, this variant can have the particular advantage that normal pacemaker operation can be resumed sooner. To realize this, suitable means should be provided for storing the threshold correlation variable value in memory and for performing a repeated comparison of the correlation variable values calculated in a calibration state with this memorized threshold value.

It will be understood that the above description of the present invention is susceptible to various modifications, changes and adaptations, and the same are intended to be comprehended within the meaning and range of equivalents of the appended claims.

What is claimed is:

1. A self-calibrating adaptive-rate cardiac pacemaker comprising a measuring and processing device for measuring the course over time of a physiological variable over a predetermined portion of a heart cycle and for obtaining a course parameter from the course over time; a stimulation parameter determining device connected to receive the course parameter from the measuring and processing device for determining a stimulation parameter value comprising an adaptive stimulation rate; a body sensor connected to an input of the stimulation parameter determining device, for detecting an exertion variable, which is used jointly with the course parameter by said stimulation parameter determining device to determine the stimulation parameter value; and a stimulator unit for generating and outputting stimulation pulses at the determined stimulation parameter value; said measuring and processing device being arranged to obtain a plurality of different values of the course parameter as a function of at least one setting parameter in a calibration phase; and said stimulation parameter determining device comprising a stimulation parameter calculating device for calculating a plurality of stimulation parameter selection values, each as a function of one value for the course parameter, a reference parameter calculating device, connected to receive the exertion variable from the body sensor for calculating an activity-determined reference parameter value, a comparator unit, connected to the stimulation parameter calculating device for receiving and comparing the parameter selection values with the reference parameter value, and a decision-making device, connected to an output of the comparator unit for selecting one of the values of said setting parameter of the measuring and processing device, associated with the parameter selection values, as a current value of said setting parameter to control said stimulation parameter determining device to determine a stimulation parameter in accordance with said current value.

2. The pacemaker of claim 1, wherein said measuring and processing device is arranged to measure and process the intracardial impedance as the physiological variable.

3. The pacemaker of claim 1, further comprising a sequence controller arranged for simultaneously picking up the time dependency of the plurality of parameter selection values and of the reference parameter value during said calibration phase, the parameter calculating device and the reference parameter calculating device being arranged for picking up a time dependency, and memories for storing the time dependency, and wherein the comparator unit comprises a correlation calculating unit for determining the value of a correlation variable for the time dependency of the parameter selection values and the time dependency of the reference parameter value and for outputting the correlation variable values to the decision-making device.

4. The pacemaker of claim 2, wherein said impedance measuring and processing device is arranged for determining the rise in an impedance-time curve in a scanning time interval determined by a pair of values for a starting and ending time after an stimulation pulse as a setting point.

5. The pacemaker of claim 3, wherein said stimulation parameter determining device is arranged for stepwise iterative calculation of the correlation variable and of the reference parameter value.

6. The pacemaker of claim 4, wherein said impedance measuring and processing device has a memory for storing a predetermined quantity of value pairs of starting and ending times.

7. The pacemaker of claim 1, wherein said measuring and processing device has means for smoothing transient fluctuations or position-change-dictated fluctuations of the course parameter values.

8. The pacemaker of claim 1, wherein said body sensor is an activity sensor.

9. The pacemaker of claim 1, wherein said stimulation parameter determining device is assigned a stimulation control switchover unit for selectively switching over to body sensor-controlled pacemaker operation.

* * * * *